US00PP21013P2

(12) United States Plant Patent
Hofmann

(10) Patent No.: US PP21,013 P2
(45) Date of Patent: May 25, 2010

(54) **NEW GUINEA *IMPATIENS* PLANT NAMED 'FISNICS SWEOR'**

(50) Latin Name: *Impatiens hawkeri*
Varietal Denomination: Fisnics Sweor

(75) Inventor: Birgit Christa Hofmann, Ruedesheim (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/383,041

(22) Filed: Mar. 19, 2009

(51) Int. Cl.
*A01H 5/00* (2006.01)

(52) U.S. Cl. ..... Plt./318.1

(58) Field of Classification Search ..... Plt./318.1
See application file for complete search history.

*Primary Examiner*—Susan B McCormick Ewoldt
(74) *Attorney, Agent, or Firm*—S. Matthew Edwards

(57) ABSTRACT

A New Guinea *Impatiens* plant named 'Fisnics Sweor,' particularly distinguished by the pale pink and orange-red, bi-color flowers, very dark green foliage, large, glossy leaves, about medium growth vigor, initially tight, later moderately tight, semi-spherical habit, and about mid season flowering.

1 Drawing Sheet

Latin name of the genus and species of the plant claimed: *Impatiens hawkeri.*

Varietal denomination: 'Fisnics Sweor'.

BACKGROUND OF THE NEW PLANT

The present invention comprises a New Guinea *Impatiens*, botanically known as *Impatiens hawkeri* and hereinafter referred to by the variety name 'Fisnics Sweor.'

'Fisnics Sweor' is a product of a planned breeding program. The new cultivar has light pink and orange-red, bi-colored flowers, very dark green foliage, and about medium sized plant habit.

'Fisnics Sweor' originated from a hybridization made in the summer of 2004 in a controlled breeding program in Hilllscheid, Germany. The female parent was an unpatented hybrid seedling identified as 'k04-4119-5' with red and pale pink, bi-color flower, dark green foliage, and compact plant habit.

The male parent of 'Fisnics Sweor' was an unpatented hybrid seedling identified as 'k04-4095-1' with orange-red and nearly white flower color, dark green foliage, and vigorous growth habit.

The resulting seeds were sown in November 2004, and 'Fisnics Sweor' was selected as one flowering plant within the progeny of the stated cross in the spring of 2005 in a controlled environment in Moncarapacho, Portugal.

The first act of asexual reproduction of 'Fisnics Sweor' was accomplished when vegetative cuttings were taken from the initial selection in July 2005 in a controlled environment in Moncarapacho, Portugal.

Horticultural examination of plants grown from cuttings of the plant initiated in late February of 2006 in Hillscheid, Germany, and continuing thereafter, has demonstrated that the combination of characteristics as herein disclosed for 'Fisnics Sweor' are firmly fixed and are retained through successive generations of asexual reproduction.

'Fisnics Sweor' has not been observed under all possible environmental conditions. The phenotype may vary significantly with variations in environment such as temperature, light intensity and day length.

Plant Breeder's Rights for this cultivar were applied for in Canada on Apr. 29, 2008 and in Switzerland on Mar. 20, 2008. 'Fisnics Sweor' has not been made publicly available more than one year prior to the filing of this application.

BRIEF DESCRIPTION OF DRAWING

The accompanying photographic drawing shows typical flower and foliage characteristics of 'Fisnics Sweor' with colors being as true as possible with an illustration of this type. The photographic drawing shows a flowering potted plant of the new variety.

DETAILED BOTANICAL DESCRIPTION

The measurements were taken in Hillscheid, Germany, in late August 2008 on plants that were growing outdoors. Culture of these plants had started in late February 2008 when rooted cuttings were planted into 12 cm pots, placed in the greenhouse and cultivated at a minimum temperature of 16° C. In late May plants were transplanted, three each, into 45 cm diameter containers that were placed outdoors, two containers per variety were placed along the greenhouse under light rain protection.

Color Chart used: Royal Horticultural Society Colour Chart (R.H.S.) 2001.

BRIEF SUMMARY OF INVENTION

The following observations, measurements, and comparisons describe plants grown indoors and outside in Hillscheid, Germany, and Chatelerault, France. The following traits have been repeatedly observed and are determined to be basic characteristics of the new variety. The combination of these characteristics distinguishes this New Guinea *Impatiens* as a new and distinct variety.

1. Bi-color flowers, pale pink color with strong, orange-red markings.
2. Large, nearly round flowers well above the foliage.
3. Very dark green foliage and relatively large, elliptical leaves.

4. Generally strong anthocyanin coloration, purple stems and leaf undersides.
5. About medium sized, mounding plant habit with fair branching.
6. Mid season flowering.

DIFFERENCES BETWEEN THE NEW VARIETY 'FISNICS SWEOR' AND SIMILAR VARIETIES

In comparison to 'Fisnics Sweet Orange,' U.S. Plant Pat. No. 14,736, 'Fisnics Sweor' has a pale pink petal ground color, RHS 56D, while 'Fisnics Sweet Orange' has pale salmon ground color, RHS 29C, and orange markings, RHS 33A–B, instead of orange-red striped patterns, RHS 40A. In addition, 'Fisnics Sweor' has somewhat larger flowers.

In comparison to 'Orange Neptis,' Plant Breeder's Right registration under 'Kinepor,' 'Fisnics Sweor' has somewhat larger flowers, and the orange-red flower pattern is somewhat less predominant in the flowers. Additionally, foliage of 'Fisnics Sweor' is distinctly darker green with larger leaves.

Plant:

*Form, growth and habit.*—About medium sized, semi-spherically in shape, bushy, initially tight, later only moderately tight plant habit.
*Plant height.*—30 cm.
*Plant width.*—40–45 cm.
*Number of branches.*—10.
*Propagation.*—Terminal tips for cuttings.
*Time to produce a finished flowering plant.*—About 10 weeks for a 12 cm pot.
*Time to initiate and develop roots.*—18 days or less at 22° C.

Stem:

*Color of stem.*—Reddish brown, RHS 184A, in the middle portion, deep purple, RHS 187B, near the tips.
*Length of stem.*—About 20–25 cm.
*Diameter.*—1.0–1.5 cm.
*Length of internodes.*—2–5 cm.
*Texture.*—Glabrous.

Foliage:

*Arrangement.*—Mainly in whorls.
*Immature leaf, color upper surface.*—RHS 137A, partly infused with purple tones, RHS 187A, but weaker in appearance.
*Immature leaf, color lower surface.*—Between RHS 185A and 187B.
*Mature leaf, color upper surface.*—RHS N189A.
*Mature leaf, color lower surface.*—RHS 184A.
*Leaf blade length.*—16.7 cm.
*Leaf width.*—6.3 cm.
*Shape.*—Elliptical.
*Base shape.*—Acute.
*Apex shape.*—Acuminate.
*Margin.*—Serrulate, ciliate.
*Color of veins, upper surface.*—RHS 53A.
*Color of veins, lower surface.*—RHS 60A.
*Texture.*—Smooth, leathery, glossy, glabrous.

Petiole:

*Color upper surface.*—RHS 53A.
*Color lower surface.*—RHS 60A.
*Length.*—2–3 cm.
*Diameter.*—3–4 mm.
*Texture.*—Glabrous.

Inflorescence:

*Start of flowering.*—Mid season, 9–10 weeks after planting of rooted cuttings.
*Duration of flowering.*—Continuous flowering throughout the summer, in the greenhouse year round, depending on light intensity.
*Inflorescence type.*—Flowers appear solitary in the leaf axils of the upper nodes of the stems.
*Number of flowers per node.*—3–6 open flowers and buds in various stages of development.
*Number of flower per plant.*—Approximately 12–16.
*Lastingness of individual blooms.*—About 9–12 days (at 18° C., greenhouse in springtime).
*Fragrance.*—None.

Pedicel:

*Color.*—Pale green, RHS 145B to 145C.
*Length.*—5.0–5.5 cm.
*Diameter.*—2 mm.
*Texture.*—Flexible, glabrous.

Flower:

*Form.*—Single-type, 5 petals.
*Shape of corolla.*—Slightly zygomorphic, with partly overlapping petals, flat or with the lateral petals slanting somewhat upward.
*Overall color.*—Bi-color: pale pink ground color and strong orange-red pattern of fine radial stripes and a large splotch on the upper petal.
*Ground color, upper surface.*—RHS 56D, uniform.
*2nd color, markings.*—RHS 40A.
*Lower surface.*—RHS 40D, at margins RHS 41D or lighter.
*Length of flower.*—8.2 cm.
*Width of flower.*—7.7 cm.
*Depth.*—1.0–2.0 cm.

Petals:

*Shape of banner petal.*—Obcordate.
*Lateral and lower petals.*—Obcordate.
*Apex shape.*—Emarginate.
*Base.*—Attenuate.
*Margin.*—Entire.

Petal size:

*Upper (banner) petal, length.*—3.8–4.0 cm.
*Upper petal, width.*—6.4–6.6 cm.
*Lateral petals, length.*—3.8–4.1 cm.
*Lateral petals, width.*—4.6–5.0 cm.
*Lower petals, length.*—3.7–3.9 cm.
*Lower petals, width.*—5.3–5.5 cm.

Spur:

*Position and shape.*—Elongate, curving downwardly.
*Color.*—Mainly pale green, RHS 145C.
*Length.*—6.0–6.5 cm.
*Diameter.*—3 mm near base.

Bud (just before opening):

*Shape.*—Ovoid.
*Length.*—2.1 cm.
*Diameter.*—1.5–1.7 cm.

Calyx:

*Number of sepals.*—4–5, of the upper one fused with the underside of the banner petal, 2 lateral sepals, and a large sepal (2 fused sepals) bearing the spur.
*Color of lateral sepals.*—RHS 180C.
*Shape of lateral sepals.*—Ovate with acuminate tip.
*Length of sepals.*—1.7 cm.
*Width of sepals.*—0.6–0.7 cm.

*Color of large sepal.*—RHS 51A near base, mainly RHS 55C.
*Shape of large sepal.*—Broad, ovate with cuspidate tip.
*Length of large sepal*—2.1–2.3 cm.
*Width of large sepal.*—2.2–2.3 cm.
*Margins.*—Entire.
*Texture.*—Glabrous.

Reproductive organs:
*Pistil.*—One.
*Length.*—6–7 mm.
*Ovary shape.*—Elongate, 5-celled.
*Color of ovary.*—Dark purple, RHS 187A.
*Style and stigma color.*—Purple-pink, RHS 60C.
*Androeceum.*—5 stamen, fused, the anthers hooded.
*Diameter.*—6–7 mm.
*Surface color.*—Purple-pink, RHS 67A–67B.
*Pollen amount.*—Moderate.
*Color of pollen.*—RHS 8D (whitish-yellow).
*Fertility/seed set.*—No seed set observed.

Disease/pest resistance: Disease resistance or susceptibility has not been observed on this hybrid.

What is claimed is:

1. A new and distinct variety of New Guinea *Impatiens* plant named 'Fisnics Sweor,' substantially as illustrated and described herein.

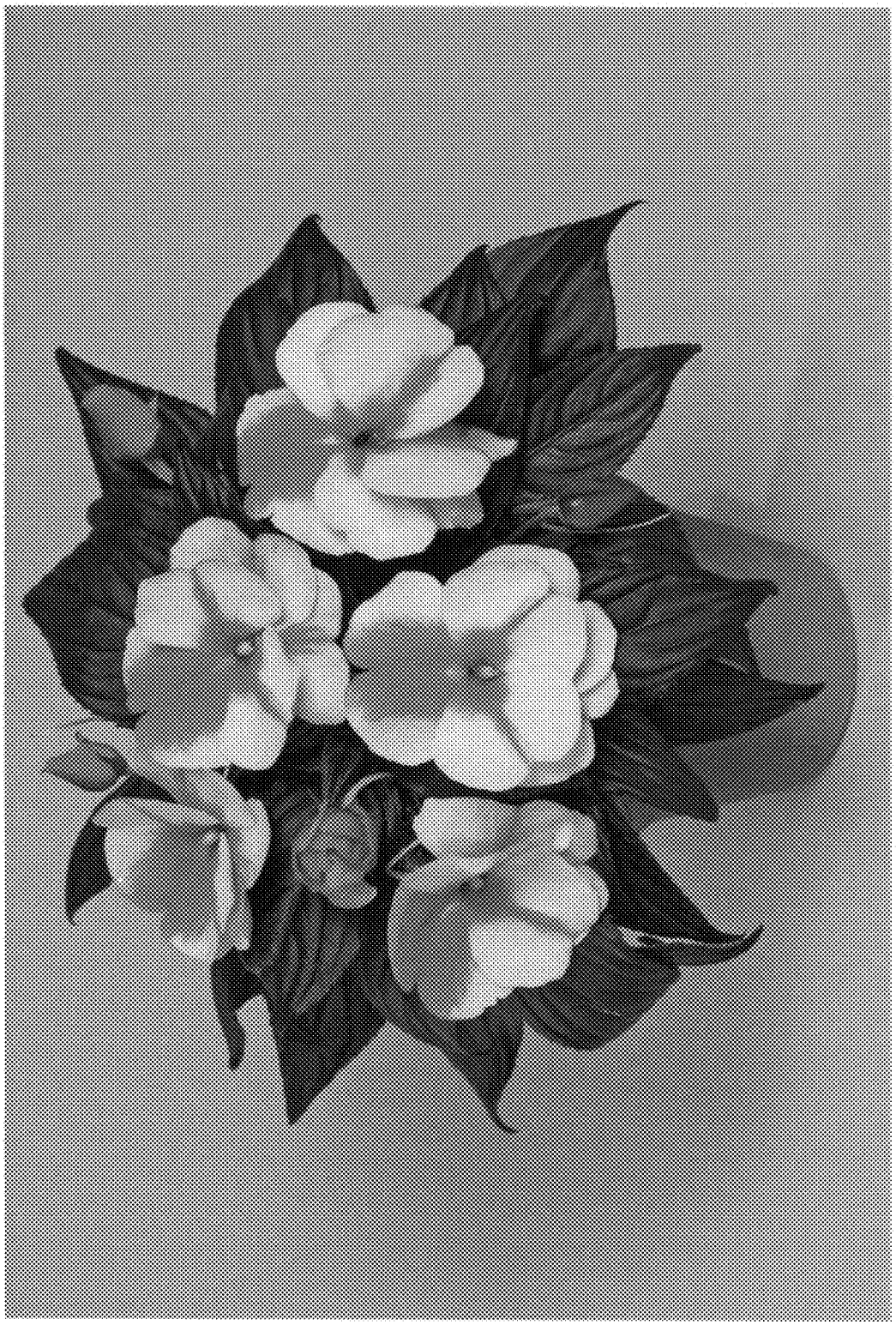

* * * * *